United States Patent [19]

McSpadden

[11] 4,299,571
[45] Nov. 10, 1981

[54] DENTAL FILE

[75] Inventor: John T. McSpadden, Johnson City, Tenn.

[73] Assignee: Inventive Technology International, Inc., Johson City, Tenn.

[21] Appl. No.: 63,436

[22] Filed: Aug. 3, 1979

[51] Int. Cl.³ .............................................. A61C 5/02
[52] U.S. Cl. .................................... 433/102; 433/122
[58] Field of Search ........................... 433/102, 81, 72

[56] References Cited

U.S. PATENT DOCUMENTS

| 636,359 | 3/1899 | Schultz | 433/102 |
| 4,165,562 | 8/1979 | Salfatti | 433/102 |
| 4,190,958 | 3/1980 | Martin et al. | 433/102 |

Primary Examiner—Robert Peshock
Attorney, Agent, or Firm—Luedeka & Fitch

[57] ABSTRACT

Disclosed is a dental file for use in cleaning out or extirpating root canals, particularly those which are curved, wherein the file which conventionally is provided with cutting or abrading flutes, typically in a spiraled manner, is also provided with a smooth, non-abrading pilot end which rides on the deep inner portion of the root canal wall and prevents the file from straightening out and causing the end thereof to "zip" or slice into the canal wall in an uncontrolled manner.

4 Claims, 3 Drawing Figures

DENTAL FILE

This invention relates to the field of root canal dentistry and in particular to novel means for cleaning and enlarging tooth root canals preparatory to compacting filler material therein. More particularly, the present invention comprises a special type file having a leading end which guides the file when the file is stressed in a curved root canal and prevents uncontrolled cutting or abrasion of the root canal through the tendency of the file to assume its straightened configuration.

In the field of root canal dentistry, one of the most important and precise mechanical operations is that of cleaning or extirpating the root canal in a carefully controlled manner which gives a properly dimensioned cavity. This step is important in order to allow proper filling of the root canal void in a homogeneous three-dimensional manner such that leakage or communication between the root canal system and the surrounding and supporting tissues of the tooth is prevented.

In performing the cleaning and enlarging of the root canal, instruments called files are used, the most common being the Hedstrom file. These files are made by machine grinding flutes into tapered, rod shaped, metal stock to form a series of intersecting cones, the diameters of which increase, moving from the tip toward the handle end. The Hedstrom file may be characterized, then, as a tapered, pointed metal instrument, hand or powered operated, with spiral cutting edges that are arranged so that cutting occurs on a pulling stroke. These files are used to clean and enlarge the root canal by a cutting or an abrasive action and a fuller description of their use is given in the dental text, "Pathways of the Pulp," by Stephen Cohen and Richard Burns and published by The C. V. Mosby Co, St. Louis, 1976, and in the brochure of SYBRON/Kerr Company, entitled "Kerr: Master Crafted Edodontic Instruments/Materials," 28200 Wick Road, Romulus, Mich.

One of the complications that often occurs in using the Hedstrom file, especially when power operated, is "zipping" the canal. A zip is a cut made in the side of the root and typically occurs when the file is used in a curved canal and tends to assume its straight configuration. The zip actually may perforate the wall of the root causing injury of the supporting tissues of the tooth.

The present invention has as its objects to reduce the technical difficulties in cleaning and enlarging root canals, and to provide convenient, substantially automatic, and easily manipulatable means for performing the operation.

These and further objects hereinafter appearing have been attained in accordance with the present invention through the discovery of a unique and unobvious cleaning and enlarging tool, hereinafter termed "file," which is easily operable with much more efficiency and speed, either by hand or by power operator, than known files.

The invention is defined as a file body having a plurality of flutes, either separate or continuous spiraled, along a working portion of said body, and a substantially smooth end portion on said body adapted to slide in a root canal and pilot the file in accordance with the configuration of the root canal. The diameter of the flutes preferably are progressively diminished along the working portion toward the pilot end to provide a taper.

The invention will be further understood from the following description and drawing wherein.

Figure 2:
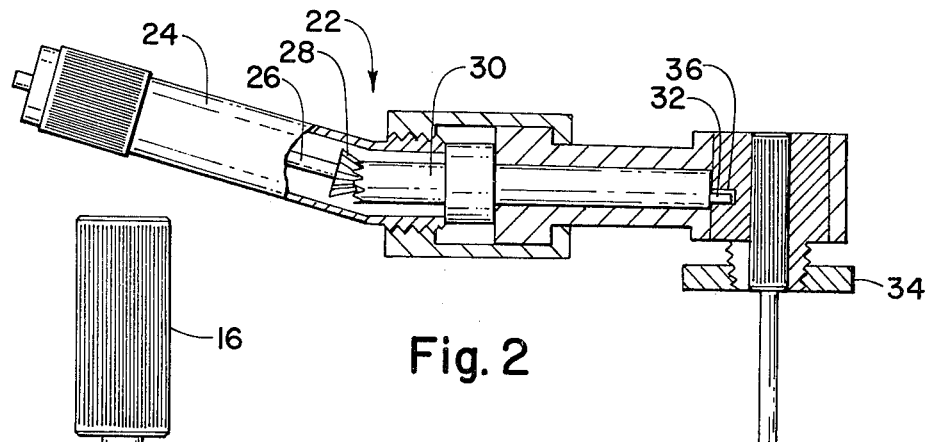
FIG. 2 is a partial cross-sectional view of the file in use and mounted in a power unit.

Referring to the drawing, the file, generally designated 10 and being about 1 to 2 inches long, comprises a body having a shank portion 12 and a working portion 14, each of which may have various cross-sectional configurations including rectangular, triangular, but preferably round.

The "anti-zip" feature of the present file is provided by the smooth, preferably round, pilot end 15 which may be tapered as shown or straight, and which extends for any convenient distance, e.g., about 1 to 3 mm., preferably about 1.25 to about 2.5 mm. beyond the termination of the flutes or shoulders 18. Pilot 15 should be sufficiently long to allow substantial and practical longitudinal movement of the file without becoming dislodged from the chosen pilot portion of the root canal itself.

Figure 1:
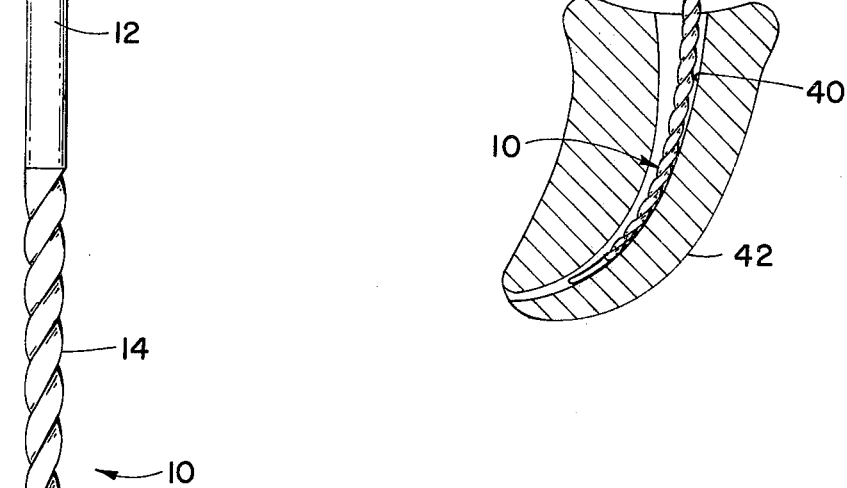
FIG. 1 is a partial cross-sectional view of the tapered, continuous spiraled flute embodiment of the present file.

An enlarged end 16 on the body, which may be an enlarged portion of handle of the shank, may be provided for manual or chuck gripping as hereinafter described. A plurality of shoulders 18 are provided on the working portion and may circumscribe the body in a continuous, uniform manner as shown in FIG. 1, or may be irregular, e.g., discontinuous and/or undulating. These shoulders preferably number between about 0.1 to about 5.0 per millimeter, and most preferably between about 0.5 and about 2.0 per millimeter. The shoulders are cut or otherwise formed such that longitudinal motion of the file will cut or abrade the walls of the canal. For this purpose, the shoulders may be slightly undercut either toward or away from the handle 16 as desired to provide the abrading action either on the push stroke or pull stroke, or both, of the file. Severe undercuts, such as 45° or so, are unnecessary and not preferred. The angle of shoulders 18 of from about 70° to 110° is entirely adequate to achieve good cutting or abrading of the root canal wall. The angle preferably is from about 90° to about 80°. The shoulder diameters may be progressively reduced as shown in the drawing to provide a tapered tool or the diameters may be the same to give a straight file. When spiraled, the aforesaid number of shoulders per millimeter refers to the number of complete spirals per millimeter. The outer diameter of the shoulders may vary between, for example, about 2.5 mm. and about 0.2 mm. as required by the various stages of the filing procedure and also for different size root canals. The inside diameter of the shoulders should be sufficient to provide adequate strength to the file body, while allowing adequate surface area for the shoulders to function properly. The diameters may be reduced by a proportional amount for the tapered tools. Preferred materials for the tool are stainless and carbon steel. The enlarged end or handle 16 is typically molded plastic but may be of any structural material including metal and may be integral with the shank and of any size. Usually small plastic handles are molded onto the root canal tools such as compactors, condensers, files, pluggers, reamers, and the like, and such may be done with the present tool.

As shown in FIG. 2, the tool may be power actuated by mounting in a hand-held actuator such as 22. Such actuators generally comprise a housing 24 in which is mounted a drive shaft 26, drive gear 28, power take-off shaft and gear assembly 30, actuator cam 32, and reciprocative chuck or tool holder 34 provided with a cam follower recess 36 which is oversized to allow for the angular, reciprocating rotation. Generally a linear reciprocation travel for the chuck of about 2.0 mm., and an angular reciprocation of about 20°, is quite functional. Such construction is typical for these power actuators. Shaft 26 may be connected, for example, by a suitable chuck to the output shaft of an air driven or electric motor which may be powered from a wall outlet or batteries, and provided with any necessary gear reduction to give the proper reciprocation frequency for the obturating tool. The type of power actuator for the tool also is not limiting of the invention in any way, and the aforementioned textbook may be referred to also for a description of some of the available reciprocating power actuators.

Figure 3:
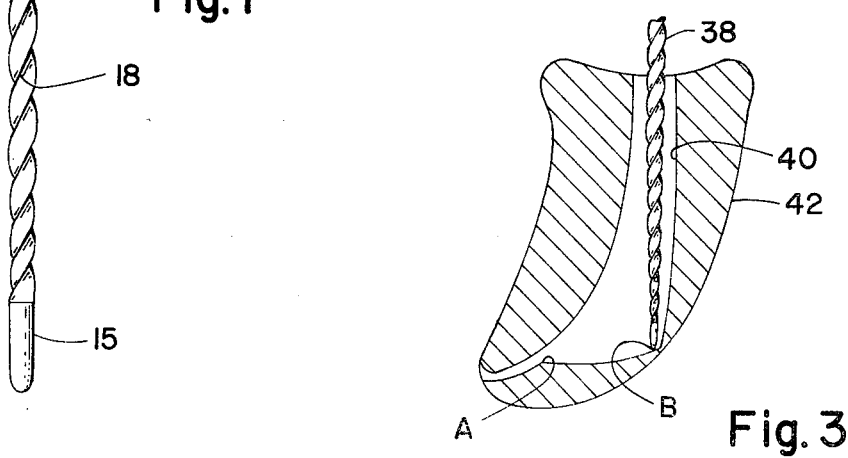
FIG. 3 is a partial cross-sectional view depicting the zip problem associated with the use of conventional files.

Referring to FIG. 3, a conventional file 38 is shown and does not have the smooth pilot end. As a result, the root canal wall 40 of tooth 42 has been grossly enlarged from point A to point B in a slitting or zip-like manner through the natural tendency of the file to assume its normal straight shape, unrestrained by any non-abrading segment of the file. In contrast, the pilot end 15 of applicant's file as shown in FIG. 2 does not abrade the root canal wall and consequently does not allow the file to uncontrollably slit or gouge the canal wall. The conventional portions of the file, however, are still able to cut the walls of the canal, but now in a controlled manner, retaining the natural curvature thereof.

The invention has been described in detail with particular reference to certain preferred embodiments thereof, but it will be understood that variations and modifications can be effected within the spirit and scope of the invention.

I claim:

1. A root canal file comprising an elongated body having a shank portion and a working portion, cutting shoulder means on said working portion circumscribing said body in a continuous manner and numbering from about 0.1 to about 5.0 per millimeter of body length, and a smooth pilot end of from greater than about 1.0 millimeters to about 3.0 millimeters in length extending from said working portion.

2. The tool of claim 1 wherein the diameter of the shoulder means is progressively diminished toward said pilot end to provide a taper.

3. The tool of claim 1 wherein the shoulder means are combined into a screw-like continuous surface.

4. The tool of claim 1 wherein the cutting shoulder means number from about 0.1 to about 5.0 per millimeter of tool length.

* * * * *